US00PP19521P2

(12) United States Plant Patent
Ikeda et al.

(10) Patent No.: US PP19,521 P2
(45) Date of Patent: Dec. 2, 2008

(54) ***FUCHSIA* PLANT NAMED 'SANIFREHO'**

(50) Latin Name: *Fuchsia×hybrida*
Varietal Denomination: Sanifreho

(75) Inventors: Mito Ikeda, Hyogo (JP); Hidefumi Funakoshi, Hyogo (JP); Yasuo Kishimoto, Hyogo (JP); Yasuyuki Murakami, Shiga (JP)

(73) Assignees: Suntory Flowers Limited, Tokyo (JP); Nishinomiya City, Hyogo (JP)

( * ) Notice: Subject to any disclaimer, the term of this patent is extended or adjusted under 35 U.S.C. 154(b) by 0 days.

(21) Appl. No.: 11/998,804

(22) Filed: Nov. 30, 2007

(51) Int. Cl.
*A01H 5/00* (2006.01)

(52) U.S. Cl. ..... Plt./300

(58) Field of Classification Search ..... Plt./300
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Fuchsia* plant named 'Sanifreho', characterized by its compact and semi-upright growth habit; freely branching plant habit; bright red and white bi-colored double flowers; freely and continuous flowering habit; long flowering period; and tolerance to low and high temperatures.

1 Drawing Sheet

Botanical designation: *Fuchsia×hybrida.*
Cultivar denomination: 'Sanifreho'.

BACKGROUND OF THE INVENTION

The present invention relates to a new and distinct cultivar of *Fuchsia,* botanically known as *Fuchsia×hybrida* and hereinafter referred to by the name 'Sanifreho'.

The new *Fuchsia* is a product of a planned breeding program conducted by the Inventors in Nishinomiya, Hyogo, Japan. The objective of the breeding program is to create new outwardly arching *Fuchsia* cultivars with numerous flowers and attractive flower coloration and form.

The new *Fuchsia* originated from a cross-pollination made by the Inventors in 2002 in Nishinomiya, Hyogo, Japan of a proprietary selection of *Fuchsia×hybrida* identified as code number aoq-1, not patented, as the female, or seed, parent with a proprietary selection of *Fuchsia×hybrida* identified as code number aez-42, not patented, as the male, or pollen, parent. The new *Fuchsia* was discovered and selected by the Inventor as a single flowering plant within the progeny of the stated cross-pollination in a controlled environment in Nishinomiya, Hyogo, Japan.

Asexual reproduction of the new *Fuchsia* by terminal cuttings in a controlled environment in Nishinomiya, Hyogo, Japan and Higashiomi, Shiga, Japan, since January, 2003, has shown that the unique features of this new *Fuchsia* are stable and reproduced true to type in successive generations.

SUMMARY OF THE INVENTION

The cultivar Sanifreho has not been observed under all possible environmental conditions. The phenotype may vary somewhat with variations in environmental and cultural practices such as temperature and light intensity without, however, any variance in genotype.

The following traits have been repeatedly observed and are determined to be the unique characteristics of 'Sanifreho'. These characteristics in combination distinguish 'Sanifreho' as a new and distinct cultivar of *Fuchsia:*

1. Compact and semi-upright growth habit.
2. Freely branching plant habit; bushy habit.
3. Bright red and white bi-colored double flowers.
4. Freely and continuous flowering habit; long flowering period.
5. Tolerant to low and high temperatures.

Plants of the new *Fuchsia* differ primarily from plants of the female parent selection in the following characteristics:

1. Plants of the new *Fuchsia* have shorter calyx tubes than plants of the female parent selection.
2. Plants of the new *Fuchsia* and the female parent selection differ in flower color as plants of the female parent selection have light pink-colored flowers.

Plants of the new *Fuchsia* differ primarily from plants of the male parent selection in the following characteristics:

1. Plants of the new Petunia are more upright than and not as outwardly spreading as plants of the male parent selection.
2. Plants of the new *Fuchsia* have shorter sepals than plants of the male parent selection.
3. Plants of the new *Fuchsia* and the male parent selection differ in flower coloration and form as plants of the male parent selection have single purple-colored flowers.

Plants of the new *Fuchsia* can also be compared to plants of the cultivar Sanicomf, disclosed in U.S. Plant Pat. No. 10,453. In side-by-side comparisons conducted in Nishinomiya, Hyogo, Japan, plants of the new *Fuchsia* and the cultivar Sanicomf differed in the following characteristics:

1. Plants of the new *Fuchsia* had thicker stems than plants of the cultivar Sanicomf.
2. Plants of the new *Fuchsia* had larger leaves than plants of the cultivar Sanicomf.
3. Plants of the new *Fuchsia* had larger flowers than plants of the cultivar Sanicomf.
4. Plants of the new *Fuchsia* had double flowers whereas plants of the cultivar Sanicomf had single flowers.

5. Plants of the new *Fuchsia* and the cultivar Sanicomf differed in petal color as plants of the cultivar Sanicomf had red purple-colored petals.
6. Plants of the new *Fuchsia* had broader sepals than plants of the cultivar Sanicomf.
7. Plants of the new *Fuchsia* had longer peduncles than plants of the cultivar Sanicomf.

BRIEF DESCRIPTION OF THE PHOTOGRAPHS

The accompanying colored photographs illustrate the overall appearance of the new *Fuchsia,* showing the colors as true as it is reasonably possible to obtain in colored reproductions of this type. Colors in the photographs may differ slightly from the color values cited in the detailed botanical description which accurately describe the colors of the new *Fuchsia.*

The photograph at the top of the sheet comprises a side perspective view of a typical flowering plant of 'Sanifreho' grown in a container.

The photograph at the bottom of the sheet is a close-up of typical flowers of 'Sanifreho'.

DETAILED BOTANICAL DESCRIPTION

The aforementioned photographs and following observations, measurements and values describe plants grown in Nishinomiya, Hyogo, Japan, under commercial practice in a polyethylene-covered greenhouse with day temperatures ranging from 15° C. to 32° C. and night temperatures ranging from 10° C. to 25° C. Plants were grown for about one year with one plant per 13.5-cm container. In the following description, color references are made to The Royal Horticultural Society Colour Chart, 2001 Edition, except where general terms of ordinary dictionary significance are used.

Botanical classification: *Fuchsia×hybrida* cultivar Sanifreho.

Parentage:

*Female, or seed, parent.*—Proprietary selection of *Fuchsia×hybrida* identified as code number aoq-1, not patented.

*Male, or pollen, parent.*—Proprietary selection of *Fuchsia×hybrida* identified as code number aez-42, not patented.

Propagation:

*Type.*—By terminal cuttings.

*Time to initiate roots.*—About one week at temperatures of 20° C.

*Time to produce a rooted young plant.*—About three weeks at temperatures of 20° C.

*Root description.*—Fine, fibrous; yellowish white in color.

*Rooting habit.*—Freely branching.

Plant description:

*Plant and growth habit.*—Semi-upright and compact plant habit; mounding. Freely branching; with lateral branches developing potentially at every node; bushy habit. Vigorous growth habit.

*Plant height.*—About 35 cm.

*Plant diameter.*—About 35 cm.

Lateral branch description:

*Length.*—About 15 cm.

*Diameter.*—About 3.4 mm.

*Internode length.*—About 2 cm.

*Strength.*—Strong.

*Aspect.*—Initially upright to outwardly arching.

*Texture.*—Pubescent.

*Color.*—Close to N79B.

Foliage description:

*Arrangement.*—Opposite, simple.

*Length.*—About 6.7 cm.

*Width.*—About 3.6 cm.

*Shape.*—Ovate.

*Apex.*—Acute.

*Base.*—Obtuse.

*Margin.*—Entire.

*Texture, upper and lower surfaces.*—Sparsely pubescent.

*Venation pattern.*—Pinnate; reticulate.

*Color.*—Developing foliage, upper surface: Close to 146A. Developing foliage, lower surface: Close to 147B. Fully expanded foliage, upper surface: Close to 146B; venation, close to 146B. Fully expanded foliage, lower surface: Close to 147B; venation, close to 147B.

*Petiole.*—Length: About 9.7 mm. Diameter: About 1.7 mm. Texture, upper and lower surfaces: Smooth, glabrous. Color, upper and lower surfaces: Close to N79B.

Flower description:

*Flower arrangement and habit.*—Double bi-colored axillary flowers. Flowers pendulous. Flowers not fragrant. Freely flowering habit with potentially two flowers per leaf axil.

*Natural flowering season.*—Long flowering period; in Japan, plants flower from spring to autumn; flowering continuous during this period. Flowers last about three to four days on the plant. Flowers not persistent.

*Flower diameter.*—About 5.1 cm.

*Flower height (depth).*—About 3.7 cm.

*Flower buds.*—Shape: Lenticular. Length: About 2.9 cm. Diameter: About 1.4 cm. Color: Close to 50A.

*Petals.*—Arrangement: Typically 18 to 24 in two to three whorls. Length: About 2.1 cm. Width: About 2 cm. Shape: Obovate. Apex: Truncate. Base: Obtuse. Margin: Entire. Texture, upper and lower surfaces: Smooth, glabrous; satiny. Color: When opening, upper and lower surfaces: Close to N155B; venation, close to 50A. Fully opened, upper and lower surfaces: Close to N155B.

*Sepals.*—Arrangement: Calyx star-shaped with four sepals fused at the base. Length: About 2.6 cm. Width: About 1.1 cm. Shape: Lanceolate. Apex: Acuminate. Margin: Entire. Texture, upper and lower surfaces: Smooth, glabrous; satiny. Color: When opening and fully opened, upper surface: Close to 50A. When opening and fully opened, lower surface: Close to 50A.

*Peduncles.*—Length: About 2.3 cm. Diameter: About 1 mm. Angle: Arching. Strength: Moderately strong. Texture: Sparsely pubescent. Color: Close to 144A.

*Reproductive organs.*—Stamens: Quantity: Eight per flower. Anther shape: Ellipsoidal. Anther size: About 4.8 mm by 1.6 mm. Anther color: Close to 61B. Pollen amount: Moderate. Pollen color: Close to 2D. Pistils: Quantity: One per flower. Pistil length: About 6.2 cm. Style color: Close to N57A. Stigma shape: Ellipsoidal. Stigma color: Close to 53C. Ovary color: Close to 144A.

*Seed/fruit.*—Seed and fruit development have not been observed on plants of the new *Fuchsia.*

Temperature tolerance: Plants of the new *Fuchsia* have good temperature tolerance and have been observed to tolerate temperatures ranging from about −2° C. to about 33° C.

Pathogen/pest resistance: Plants of the new *Fuchsia* have not been observed to be resistant to pests and pathogens common to *Fuchsia*.

It is claimed:

1. A new and distinct *Fuchsia* plant named 'Sanifreho' as illustrated and described.

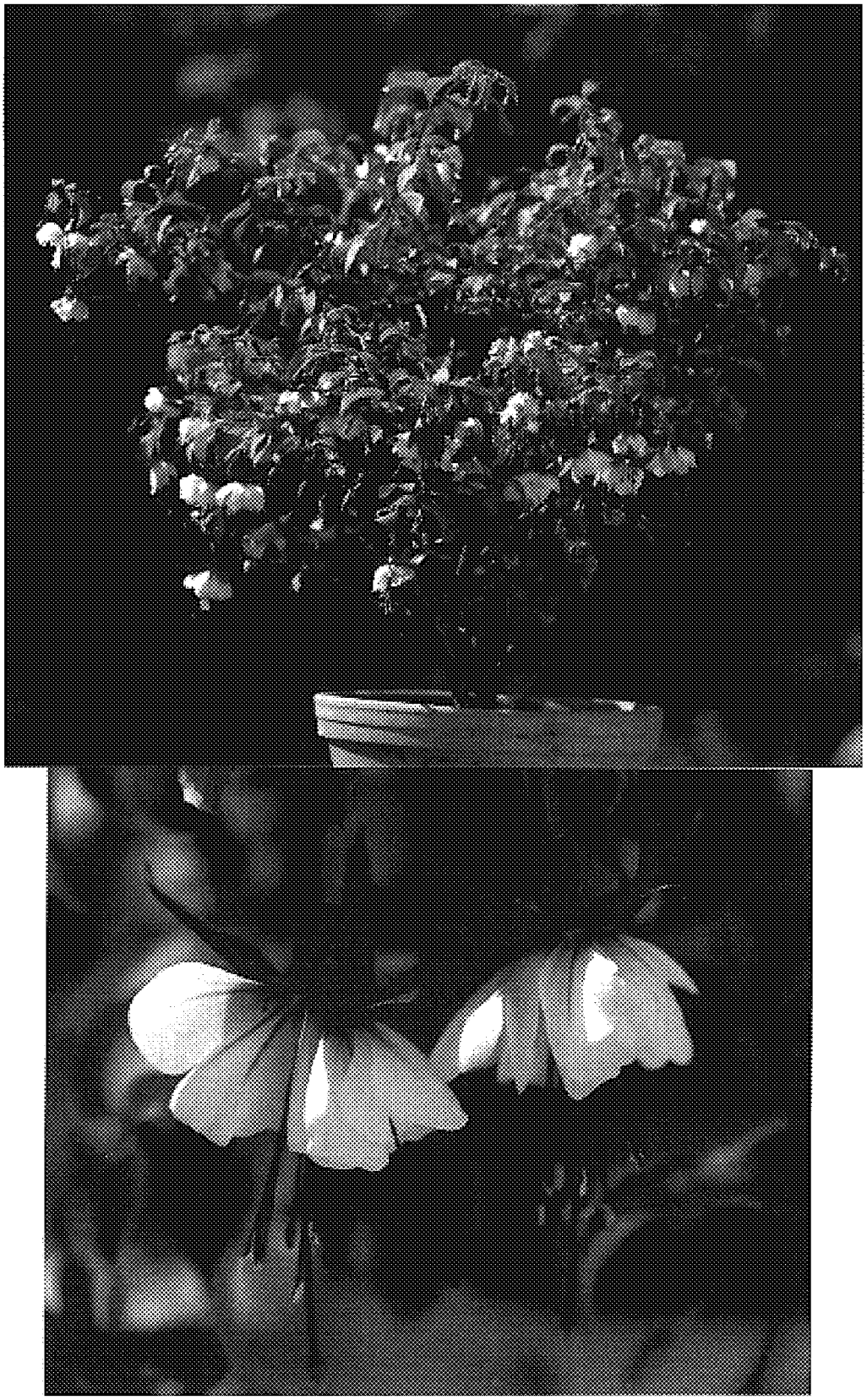

* * * * *